United States Patent [19]

Isshiki et al.

[11] Patent Number: 5,635,395
[45] Date of Patent: Jun. 3, 1997

[54] OPTICALLY ACTIVE 1,4-DIHYDROPYRIDINE COMPOUNDS AND THE MICROBIAL PROCESS FOR THE STEREOSELECTION THEREOF

[75] Inventors: Kunio Isshiki, Chigasaki; Takashi Nakashima, Yokohama; Takeo Yoshioka, Ayase; Hiroshi Tsunekawa, Fujisawa; Takashi Adachi; Tomomi Ota, both of Tokyo, all of Japan

[73] Assignees: Mercian Corporation; Taisho Pharmaceutical Co., Ltd., both of Japan

[21] Appl. No.: 387,750

[22] PCT Filed: Aug. 31, 1993

[86] PCT No.: PCT/JP93/01222

§ 371 Date: Feb. 21, 1995

§ 102(e) Date: Feb. 21, 1995

[87] PCT Pub. No.: WO94/05637

PCT Pub. Date: Mar. 17, 1994

[30] Foreign Application Priority Data

Aug. 31, 1992 [JP] Japan ..................... 4-231877

[51] Int. Cl.$^6$ .................. C12P 41/00; C07D 213/803; A01N 43/40
[52] U.S. Cl. .................. 435/280; 546/321; 514/356; 435/122; 435/136
[58] Field of Search .................. 435/280, 122, 435/136; 514/356; 546/321

[56] References Cited

U.S. PATENT DOCUMENTS 5,100,892 3/1992 Wheeler ..................... 514/252
5,234,821 8/1993 Achiwa ..................... 435/41
5,395,941 3/1995 Isshiki et al. ..................... 546/268

FOREIGN PATENT DOCUMENTS

| 0474129 | 8/1991 | European Pat. Off. |
| 64-60398 | 3/1989 | Japan. |
| 4299994 | 10/1992 | Japan. |
| 8402132 | 7/1984 | WIPO. |

OTHER PUBLICATIONS

Patent Abstracts of Japan, vol. 17, No. 409, 30 Jul. 93 JP 5-84089.

Adachi T et al., Tetrahedron: Asymmetry 4(9):2061–68 (1993).

*Primary Examiner*—David M. Naff
*Assistant Examiner*—S. Saucier
*Attorney, Agent, or Firm*—Lorusso & Loud

[57] ABSTRACT

(4R)-3-(Substituted aminoalkyl)oxycarbonyl-1,4-dihydro-2,6-dimethyl-4-(nitrophenyl)pyridine-5-carboxylic acids can be prepared efficiently, by reacting bis(substituted aminoalkyl) 1,4-dihydro-2,6-dimethyl-4-(nitrophenyl)pyridine-3,5-dicarboxylates with a microorganism capable of asymmetric hydrolysis and belonging to the genus Streptomyces, the genus Paecilomyces, the genus Botryodioplodia, the genus Alternaria or the genus Helminthosporium, or a treated product thereof. The compounds are extremely useful as important intermediates for preparation of pharmaceuticals useful for the prevention and treatment of angina pectoris, hypertension, etc.

3 Claims, No Drawings

OPTICALLY ACTIVE 1,4-DIHYDROPYRIDINE COMPOUNDS AND THE MICROBIAL PROCESS FOR THE STEREOSELECTION THEREOF

TECHNICAL FIELD

The present invention relates to intermediate compounds for optically active 1,4-dihydropyridine derivatives which are useful for the prevention and treatment of ischemic heart diseases or hypertension, and to a process for producing the intermediate compounds.

BACKGROUND ART

A 1,4-dihydropyridine compound which contains two different carboxylic acid esters each other at the 3- and 5-positions of the dihydropyridine ring possesses an asymmetric carbon atom at the 4-position thereof and thus has two optical isomers. It is reported that recent studies on biological properties of these optically active compounds reveal differences of the isomers in pharmacological activity, kinetics in vivo and safety (K. Tamazawa et al., J. Med. Chem., 29, 2504 (1986)). Where these compounds with an asymmetric carbon atom are employed as pharmaceuticals, it has been a general tendency to administer only one of the isomers that is preferable as a pharmaceutical, under such a consensus that any undesirable load should not be borne to the living body. From such a viewpoint, studies have been focused on a process for preparing optically active 1,4-dihydropyridine derivatives. As a conventional process for synthesis of optically active 1,4-dihydropyridine derivatives, there is known a process for introducing a desired ester residue into a (4R)-1,4-dihydropyridinecarboxylic acid mono-ester as an intermediate (A. Ashimori et al., Chem. Pharm. Bull., 39, 108 (1991)). For preparing this optically active intermediate, (4R)-1,4-dihydropyridine-3,5-dicarboxylic acid mono-ester, there are known the chemical process by Shibanuma et al. (Chem. Pharm. Bull., 28, 2809 (1980)) and the enzymatic methods by Achiwa et al. (Tetrahedron Letters, 32, 5805 (1991)) and by Charles J. Sih et al. (Tetrahedron Letters, 32, 3465 (1991)). However, any method for asymmetric direct hydrolysis of diesters by microbiological technique is not disclosed in these publications.

The chemical synthesis of optically active (4R)-1,4-dihydropyridine-3,5-dicarboxylic acid mono-ester described above encounters disadvantages that not only the process requires a protective group for the amino group on the dihydropyridine ring but the formed mono-carboxylic acid racemate requires optical resolution since the reaction is not asymmetric hydrolysis.

On the other hand, the process by Achiwa et al. comprises using as a substrate a dihydropyridine ester derivative having pivaloyloxymethyl at the 3- and 5-positions of the dihydropyridine ring, enzymatically hydrolyzing one of the esters asymmetrically to form an optically active dihydropyridine monocarboxylic acid derivative as an intermediate for synthesis of pharmaceuticals. However, this process involves a defect that the overall yield is not very good, because the process requires a number of steps such as synthesis of the substrate, conversion of pivaloyloxymethyl into other substituents to form compounds useful as pharmaceuticals.

According to the process of Sih et al. acetoxymethyl ester is used instead of pivaloyloxymethyl ester in the process of Achiwa et al. Both processes are basically the same.

It has thus been desired to develop a process for efficiently preparing optically active (4R)-1,4-dihydropyridine 3,5-dicarboxylic acid mono-esters.

DISCLOSURE OF INVENTION

As a result of extensive investigations to solve the problems described above, the present inventors have found a process for efficiently preparing (4R)-1,4-dihydropyridine-3,5-dicarboxylic acid mono-ester derivatives, utilizing a microorganism. The present invention has thus been accomplished.

That is, the present invention provides a process for preparing an optically active (4R)-1,4-dihydro-2,6-dimethyl-4-(nitrophenyl)pyridine-3,5 -dicarboxylic acid mono-ester derivative which comprises reacting a compound represented by formula (I) below:

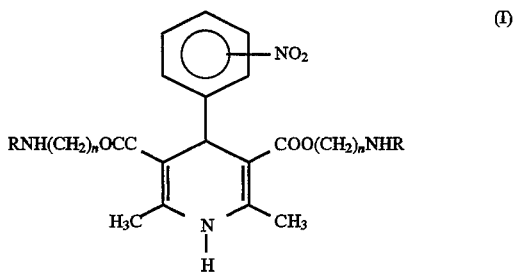

wherein R represents a lower alkanoyl group, a heterocyclic carbonyl group, a halo-substituted acetyl group, an alkoxyacetyl group, an aryloxyacetyl group, a substituted or unsubstituted phenyl-lower alkanoyl group, a phenyl-substituted or unsubstituted lower alkenoyl group, an alkoxy or alkenyloxycarbonyl group, an aralkyloxycarbonyl group or an organic sulfonyl group; and n represents an integer of 2 to 4, or a salt thereof with a microorganism capable of asymmetric hydrolysis and belonging to the genus Streptomyces, the genus Paecilomyces, the genus Botryodioplodia, the genus Alternatia or the genus Helminthosporium, or a treated product thereof, and collecting the resulting optically active 1,4-dihydropyridine compound represented by formula (II) below:

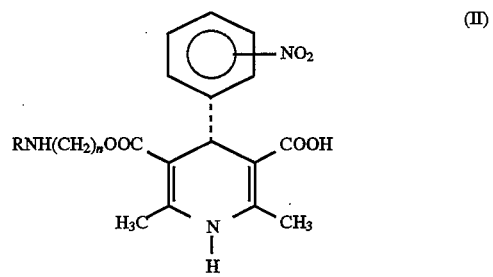

wherein R and n have the same significance as defined above, or a salt thereof.

The present invention also provides a 1,4-dihydropyridine compound represented by general formula (III) below:

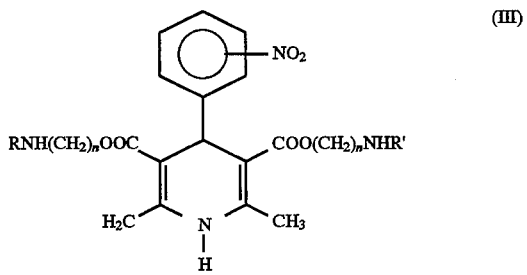

wherein R' represents a lower alkanoyl group and n represents an integer of 2 to 4.

The present invention further provides an optically active 1,4-dihydropyridine compound represented by general formula (IV) below:

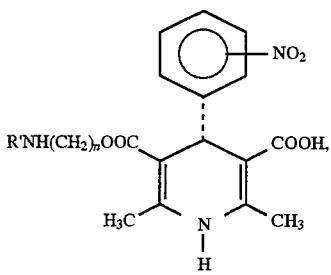
(IV)

wherein R' represents a lower alkanoyl group and n represents an integer of 2 to 4, or a salt thereof.

BEST MODE FOR CARRYING OUT THE INVENTION

In the general formulae (I) and (II) described above, R represents a lower alkanoyl group such as formyl, acetyl, propionyl, butyryl, isobutyryl, valeryl, isovaleryl, etc.; a heterocyclic carbonyl group such as picolinoyl, nicotinoyl, isonicotinoyl, nipecotinoyl, quinolinoyl, quinoxalinoyl, phenazinoyl, etc.: a halo-substituted acetyl group such as trifluoroacetyl, chloroacetyl, dichloroacetyl, trichloroacetyl, bromoacetyl, dibromoacetyl, etc.; an alkoxyacetyl group such as methoxyacetyl, ethoxyacetyl, etc.; an aryloxyacetyl group such as phenoxyacetyl, naphthyloxyacetyl, etc.; a substituted or unsubstituted phenyl-lower alkanoyl group such as phenylacetyl, methoxyphenylacetyl, phenylpropionyl, etc.; a phenyl-substituted or unsubstituted lower alkenoyl group such as crotonoyl, cinnamoyl, etc.; an alkoxy or alkenyloxycarbonyl group such as methoxycarbonyl, ethoxycarbonyl, tert-butoxycarbonyl, allyloxycarbonyl, etc.; an aralkyloxycarbonyl group such as benzyloxycarbonyl, etc.; an organic sulfonyl group such as methanesulfonyl, benzenesulfonyl, benzylsulfonyl, toluenesulfonyl, etc.

The position of nitro group substituted on the phenyl group at the 4-position is not limited but may be any one of the 2-, 3- and 4-positions.

The starting compound of formula (I) which can be used for the process of the present invention using a microorganism may also be used in the form of its salts. As such salts, there may be used addition salts of organic acids such as acetic acid, tartaric acid, benzenesulfonic acid, etc., addition salts of inorganic acids such as hydrochloric acid, sulfuric acid, etc.

The starting compound shown by formula (I) can be prepared in a conventional manner. That is, the compound of formula (I) can be prepared by reacting an ethanolamine derivative, 3-aminopropanol derivative or 4-aminobutanol derivative, in which the amino group is protected and which is represented by formula (V) below:

(V)

wherein R represents a lower alkanoyl group, a heterocyclic carbonyl group, a halo-substituted acetyl group, an alkoxyacetyl group, an aryloxyacetyl group, a substituted or unsubstituted phenyl-lower alkanoyl group, a phenyl-substituted or unsubstituted lower alkenoyl group, an alkoxy or alkenyloxycarbonyl group, an aralkyloxycarbonyl group or an organic sulfonyl group; and n represents an integer of 2 to 4, with diketene; and condensing the resulting acetoacetic acid ester represented by formula (VI) below:

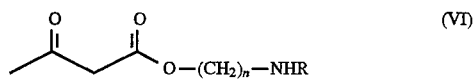
(VI)

wherein R and n have the same significance as defined above, with nitrobenzaldehyde in the presence of ammonia, while heating. Alternatively, the compound of formula (I) may also be prepared by condensing the acetoacetic acid ester represented by formula (VI) with nitrobenzaldehyde, and then condensing the resulting α-benzylidene-β-keto-ester represented by formula (VII) below:

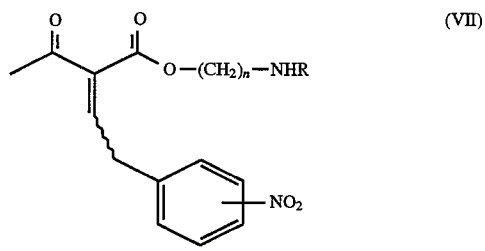
(VII)

wherein R and n have the same significance as defined above, with the acetoacetic acid ester represented by general formula (VI) in the presence of ammonia. Furthermore, the starting compound of formula (I) may also be prepared by reacting the acetoacetic acid ester represented by general formula (VI) with ammonia, and then condensing the resulting β-aminocrotonic acid ester represented by formula (VIII) below:

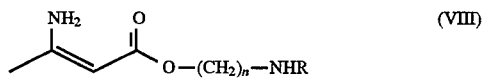
(VIII)

wherein R and n have the same significance as defined above, with nitobenzaldehyde and the acetoacetic acid ester represented by general formula (VI).

The present invention also provides a novel 1,4-dihydropyridine compound which corresponds to a compound of general formula (I) wherein R is a lower alkanoyl group and which is represented by formula (III) below:

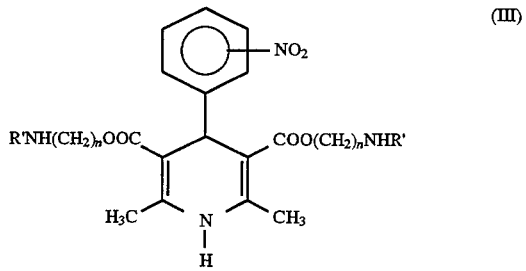
(III)

wherein R' represents a lower alkanoyl group and n represents an integer of 2 to 4. The present invention further provides a novel optically active 1,4-dihydropyridine compound shown by formula (IV) below:

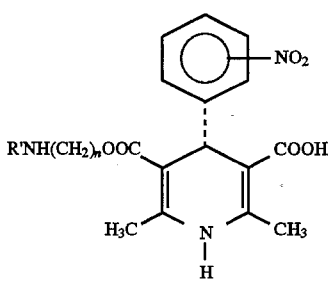

wherein R' and n have the same significance as defined above, or a salt thereof, which is produced by the process comprising subjecting the compound of formula (III) described above to the aforesaid reaction using a microorganism.

As the microorganism which can be used for the microbial reaction above, there may be employed a microorganism capable of asymmetric hydrolysis and belonging to the genus Streptomyces, the genus Paecilomyces, the genus Botryodioplodia, the genus Alternaria or the genus Helminthosporium. Examples of such microorganisms include strains FI-4, FI-741, FI-1007 and A-914. Morphological properties of these bacteria are shown below. Strain FI-4:

The strain forms cotton-like, light grayish white hyphae on potato dextrose agar medium; with the progress of incubation, the substrate turns black grey. Conidia are of polo type extending from pores at the top of conidiophores, separated by septum and take the shape of bricks laid. The conidia are round at the bottom and sharp at the top, with a brown color.

Strain FI-741:

The strain forms well-grown white cotton-like hyphae on potato dextrose agar medium; with the progress of incubation, the substrate turns brown. Conidia are formed in spherical organ termed pycnidium with open top. Conidia are somewhat long and smooth but not viscous. When matured, conidia turn brown and the cell walls are thickened.

Strain FI-1007:

The strain forms grayish white hyphae on potato dextrose agar medium; with the progress of incubation, the substrate turns somewhat pinkish brown. Conidia are of phialo type which grow from phialide at the top of conidiophores. Conidiophores are little branched but phialides are well branched to take a shallow structure.

Based on the foregoing morphological properties, survey was made on The Genera of Fungi Sporulating in Pure Culture (J.A. von ARX, 1970). As the result, FI-4, FI-741 and FI-1007 were identified to be Alternaria sp., Botryodioplodia sp. and Paecilomyces sp., respectively.

Strain A-914:

The strain forms a firm, pale brown colony on ISP-2 agar medium. With progress of culture, the surface of the colony turns somewhat grayish green. Melanin or other diffusible dyes are not formed. Submerged mycelia well grow without forming oidium and aerial mycelia are present. Many conidiospores are borne on the aerial mycelia in a helical chain form. The surface of the conidiospores is flat.

L-Diaminopimelic acid is contained in the cell wall components. The strain cannot assimilate L-hydroxyproline. The strain is sensitive to 100 µg/ml of oleandomycin.

Based on the foregoing properties, survey was made on Bergey's Manual of Systematic Bacteriology, Volume 4. As the result, A-914 was identified to be *Streptomyces viridosporus*.

Strain FI-4 was deposited in National Institute Bioscience and Human-Technology on Mar. 18, 1993 and received FERM P-13535 as an accession number. Then the deposition was transferred into an international deposition under the Budapest Treaty on Jun. 14, 1993 and received FERM BP-4335 as an accession number.

Strains FI-741, FI-1007 and A-914 were deposited in National Institute Bioscience and Human-Technology on Jul. 29, 1992 and received FERM P-13097, FERM P-13096 and FERM P-13098 as respective accession numbers. Then the deposition was transferred into an international deposition under the Budapest Treaty on Jun. 14, 1993 and received FERM BP-4333, FERM BP-4332 and FERM BP-4334 as respective accession numbers.

Additional examples of the microorganism which may also be utilized in the present invention include Streptomyces sp. ATCC 11862 and *Helminthosporium zonatum* IFO 6678. These bacteria have been deposited in American Type Culture Collection and Fermentation Research Laboratory Foundation, respectively and are readily available.

Media in which these microorganisms are cultured are not particularly limited but may be any media conventionally employed for incubation of bacteria. As carbon sources, any sources can be used as long as the bacteria listed above can assimilate. Specific examples of the carbon sources are sugars such as glucose, fructose, sucrose, dextrin, etc.; sugar alcohols such as glycerol, sorbitol, etc.; organic acids such as fumaric acid, citric acid, etc. It is preferred that these carbon sources be added to a medium generally in the proportion of approximately 0.1 to 10%. As nitrogen sources, there are utilized, for example, ammonium salts of inorganic acids such as ammonium chloride, ammonium sulfate, ammonium phosphate, etc.; ammonium salts of organic acids such as ammonium fumarate, ammonium citrate, etc.; natural organic nitrogen sources such as meat extract, yeast extract, corn steep liquor, casein hydrolysate, etc. Among them, the organic nitrogen sources may also be used as carbon sources in most cases. It is appropriate to add these nitrogen sources generally in the proportion of 0.1 to 10%. As inorganic salts, there may be used, e.g., alkali metal salts of phosphoric acid such as potassium phosphate, sodium phosphate, etc.; alkali metal salts of chlorides such as potassium chloride, sodium chlorides, etc.; metal salts of sulfuric acid such as magnesium sulfate, ferrous sulfate, etc. It is appropriate to use the inorganic salt in the range of 0.001 to 1%.

The microorganism may be incubated in the medium mentioned above at 20° to 40° C., preferably 28° to 37° C., in the pH range of 5 to 9, preferably 6 to 8, under aerobic conditions.

The microbial reaction is carried out by reacting with the microorganism or the product obtained by a treatment of the microorganism. The reaction with the microorganism is generally a reaction with the culture broth of the microorganism. The culture broth of the microorganism includes the bacterial cells, culture supernatant and culture broth of the microorganism cultured. The product obtained by a treatment of the microorganism includes the product obtained by treating the bacterial cells of the cultured microorganism and the product obtained by treating the culture supernatant and the culture broth. The treatment products of the bacterial cells include dry cells such as lyophilized cells, spray dry cells, or cells, cell extracts and immobilized products treated with, e.g., acetone, toluene, methanol, butanol, etc. The treatment products of the supernatant and the culture broth include the concentrate, dry powders and spray dry powders obtained by treating the same. Furthermore, enzyme isolated and purified from the cells and the supernatant may also be used as the treated products.

To practice the present invention, the microorganism is inoculated on a medium and then incubated at 20° to 40° C.

for 12 to 120 hours to obtain the culture broth containing $10^6$ to $10^{10}$/ml of the microorganism. The compound of formula (I) which is a starting compound is dissolved in water or a dissolution aid and the solution is added to the culture broth generally in the final concentration of 0.5 mg/ml to 5 mg/ml followed by reaction generally at 28° C. for 18 to 72 hours. After the pH is adjusted to 5, the reaction mixture is extracted with an organic solvent such as chloroform, ethyl acetate, butyl acetate, butanol, etc. The extract is then subjected to crystallization, fractionation, precipitation, etc. to obtain the objective optically active compound of formula (II).

The dissolution aid used for the above purpose may be a variety of organic solvents. Examples of such organic solvents include acetone, methyl ethyl ketone, dimethylsulfoxide, dioxane, N,N-dimethylformamide, acetonitrile, etc. These dissolution aids may be used alone or as admixture of two or more. It is preferred to add the dissolution aid to the medium in the range of 3 to 5%.

Hereinafter the present invention is described with reference to Examples but is not deemed to be limited thereto.

EXAMPLE 1

Preparation of (4R)-1,4-dihydro-2,6-dimethyl-3-(2-nicotinoylaminoethyl)oxycarbonyl-4-(3-nitrophenyl) pyridine-5-carboxylic acid 1-1) Preparation of the title compound using *Streptomyces viridosporus* A-914

*Streptomyces viridosporus* A-914 was inoculated on 30 ml medium C (2% potato starch, 2% ESUSAN Meat, 0.5% yeast extract, 0.25% NaCl, 0.32% $CaCO_3$, 0.0005% $FeSO_4$ $7H_2O$, 0.0005% $MnSO_4$ $4H_2O$, 0.0005% $ZnSO_4$ $7H_2O$, pH 7.4) charged in a flask of 250 ml volume followed by incubation at 28° C. for 3 days. A solution of 60 mg of 1,4-dihydro-2,6-dimethyl-4-(3-nitrophenyl)pyridine-3,5-dicarboxylic acid bis(2-nicotinoylaminoethyl)ester dihydrochloride in 0.75 ml of distilled water was added to the culture broth obtained. The mixture was shaken at 28° C. for further 2 days. 1N hydrochloric acid was added to the reaction mixture to adjust pH to 5.0, followed by extraction with 30 ml of ethyl acetate. The organic layer was fractionated with 0.1N sodium hydroxide aqueous solution (20 ml×3) for back extraction. After the pH was adjusted to 5.0 by adding 1N hydrochloric acid to the aqueous layer, the mixture was fractionated and extracted with 30 ml of ethyl acetate. The organic layer was washed with saturated sodium chloride aqueous solution and then dried over anhydrous sodium sulfate. The organic phase was concentrated in vacuum. The concentrate was adsorbed onto a preparative TLC plate and developed with chloroform:methanol:acetic acid (50:5:1). The eluate showing UV absorption at Rf 0.22 was concentrated to dryness to give 18.0 mg of the desired title compound.

The optical purity of the product was analyzed by HPLC (moving phase: 0.6% isopropanol—0.01M phosphate buffer (pH 7.1), flow rate: 0.7 ml/min) using Chiral AGP (4 mm×100 mm) for optical resolution column manufactured by Daicel Industry Co., Ltd. As the result, the optical purity was 100% with residence time of 4.7 minutes.

NMR ($CDCl_3$) δ: 2.37 (3H, s), 2.39 (3H, s), 3.6–3.8 (2H, m), 4.2–4.4 (2H, m), 5.18 (1H, s), 6.74 (1H, br), 7.30 (1H, t, J=8.0 Hz), 7.43 (1H, dd, J=5.0 & 8.0 Hz), 7.62 (1H, d, J=8.0 Hz), 7.94 (1H, dd, J=2.0 & 8.0 Hz), 8.10 (1H, t, J=2.0 Hz), 8.17 (1H, dt, J=8.0 & 1.5 Hz), 8.68 (1H, dd, J=1.5 & 5.0 Hz), 8.91 (1H, d, J=1.5 Hz) FAB-MS (m/z): 467 $(M+H)^+$ 1-2) Preparation of the title compound using *Streptomyces* sp. ATCC 11862

The reaction was carried out in a manner similar to Example 1-1) except for using *Streptomyces* sp. ATCC 11862 to give 0.7 mg of the objective optically active monocarboxylic acid from 4 mg of the starting compound.

1-3) Preparation of the title compound using *Botryodioplodia* sp. FI-741

*Botryodioplodia* sp. FI-741 was inoculated on 30 ml medium FI (2% potato starch, 2% ESUSAN Meat, 0.1% $KH_2PO_4$, 0.05% $MgSO_4$ $7H_2O$, 1% glucose, 0.05% Adekanol LG109) charged in an Erlenmeyer flask of 250 ml volume. Incubation was performed at 28° C. for 3 days. A solution of 60 mg of 1,4-dihydro-2,6-dimethyl-4-(3-nitrophenyl)pyridine-3,5-dicarboxylic acid bis(2-nicotinoylaminoethyl)ester dihydrochloride in 0.75 ml of distilled water was added to the culture broth obtained. Shaking was continued for further 2 days at 28° C. Thereafter the culture broth was treated in a manner similar to Example 1-1) to give 8 mg of the title compound in an optical purity of 100%.

1-4) Preparation of the title compound using *Paecilomyces* sp. FI-1007

*Paecilomyces* sp. FI-1007 was inoculated on 30 ml medium FI (2% potato starch, 2% ESUSAN Meat, 0.1% $KH_2PO_4$, 0.05% $MgSO_4$ $7H_2O$, 1% glucose, 0.05% Adekanol LG109) charged in an Erlenmeyer flask of 250 ml volume. Incubation was performed at 28° C. for 3 days. A solution of 60 mg of 1,4-dihydro-2,6-dimethyl-4-(3-nitrophenyl)pyridine-3,5-dicarboxylic acid bis(2-nicotinoylaminoethyl)ester dihydrochloride in 0.75 ml of distilled water was added to the culture broth obtained. Shaking was continued for further 2 days at 28° C. Thereafter the culture broth was treated in a manner similar to Example 1-1) to give 10 mg of the title compound in an optical purity of 100%.

1-5) Preparation of the title compounds using other bacteria

The reaction was carried out in a manner similar to Example 1-3), except for using *Alternaria* sp. FI-4 strain and *Helminthosporium zonatum* IFO 6678 strain, respectively. The preparation of the objective monocarboxylic acid was confirmed by TLC.

EXAMPLE 2

Preparation of 1,4-dihydro-2,6-dimethyl-4-(3-nitrophenyl)pyridine-3,5-dicarboxylic acid bis(2-acetamidoethyl) ester After 0.34 ml of triethylamine was added to a solution of 25 g of N-acetylethanolamine in 100 ml of dioxane, 18.7 ml of diketene was dropwise added gradually to the mixture. Following the exothermic reaction, 8.1 ml of con. ammonium hydroxide solution and 18.3 g of m-nitrobenzaldehyde were added to the mixture, followed by heating on an oil bath of 80° C. for 17 hours while stirring.

The solvent was distilled off in vacuum. The resulting residue was purified on a column packed with 700 g of silica gel using as a developing system toluene-acetone solvent mixture (mixing ratio, 2:1) to give 24 g of the product.

NMR ($CDCl_3$) δ: 1.98 (6H, s), 2.36 (6H, s), 3.48 (2H, m), 3.60 (2H, m), 3.95 (2H, m), 4.20 (2H, m), 5.11 (1H, s), 6.67 (1H, s), 6.85 (2H, t, J=6 Hz), 7.40 (1H, t, J=8 Hz), 7.70 (1H, td, 1.2 & 8 Hz), 8.00 (1H, td, J=1.2 & 8 Hz), 8.23 (1H, t, J=2 Hz) FAB-MS (m/z): 489 $(M+H)^+$

EXAMPLE 3

Preparation of (4R)-3-(2-acetamidoethyl)oxycarbonyl-1,4-dihydro-2,6-dimethyl-4-(3-nitrophenyl)pyridine-5-carboxylic acid 3-1) Preparation of the title compound using Paecilomyces sp. FI-1007

Paecilomyces sp. FI-1007 was inoculated on 30 ml medium FI (2% potato starch, 2% ESUSAN Meat, 0.1% $KH_2PO_4$, 0.05% $MgSO_4$ $7H_2O$, 1% glucose, 0.05% Adekanol LG109) charged in an Erlenmeyer flask of 250 ml volume. Incubation was performed at 28° C. for 3 days. A solution of 60 mg of 1,4-dihydro-2,6-dimethyl-4-(3-nitrophenyl)pyridine-3,5-dicarboxylic acid bis(2-acetamidoethyl)ester in 0.75 ml of dimethylsulfoxide was added to the culture broth obtained. Shaking was continued for further 2 days at 28° C. 1N hydrochloric acid was added to the reaction mixture to adjust pH to 3.0, followed by extraction with 30 ml of ethyl acetate.

The organic layer was subjected to back extraction with 20 ml of 0.1N sodium hydroxide aqueous solution. After the pH was adjusted to 3.0, the mixture was extracted with 20 ml of ethyl acetate. The organic layer was washed with saturated sodium chloride aqueous solution and then dried over anhydrous sodium sulfate. The organic phase was concentrated. Then, the concentrate was adsorbed onto a preparative TLC plate and developed with chloroform-:methanol (7:1). The eluate showing UV absorption at Rf 0.22 was evaporated in vacuum to dryness to give 10 mg of the desired title compound.

The optical purity of the product was analyzed by HPLC (moving phase: 0.35% isopropanol—0.01M phosphate buffer (pH 4.4), flow rate: 0.8 ml/min) using Chiral AGP (4 mm×100 mm) for optical resolution column manufactured by Daicel Industry Co., Ltd. As the result, the optical purity was 100% with residence time of 14.3 minutes.

NMR ($CDCl_3$) δ: 1.91 (3H, s), 2.34 (6H, s), 3.40 (2H, t, J=5.5 Hz), 4.0–4.2 (2H, m), 5.10 (1H, s), 7.44 (1H, t, J=8.0 Hz), 7.66 (1H, td, J=1.0, 2.0 & 8.0 Hz), 7.99 (1H, td, J=1.0, 2.0 & 8.0 Hz), 8.11 (1H, t, J=2.0 Hz) FAB-MS (m/z): 404 $(M+H)^+$

The product was then treated with diazomethane. The resulting methyl ester showed the following NMR spectrum.

NMR ($CD_3OD$) δ: 1.90 (3H, s), 2.30 (3H, s), 2.33 (3H, s), 3.40 (2H, t, J=5.9 Hz), 3.63 (3H, s), 4.04 (1H, dd, J=11.4 & 5.9 Hz), 4.13 (1H, dd, J=11.4 & 5.9 Hz), 5.08 (1H, s), 7.45 (1H, t, J=8 Hz), 7.65 (1H, d, J=8 Hz), 8.00 (1H, d, J=8 Hz), 8.09 (1H, s)

The authentic (R)-form of the title compound was prepared as follows. That is, 5 mg of (S)-(+)-1,4-dihydro-2,6-dimethyl-5-methoxycarbonyl-4-(3-nitrophenyl)-3-pyridinecarboxylic acid prepared according to the method described by Shibanuma et al. (Chem. Pharm. Bull., 28(9), 2809–2812 (1980)) was dissolved in 0.5 ml of tetrahydrofuran. Then 2 μl of isobutyl chloroformate was added to the solution. After stirring for 10 minutes, 6 μl of triethylamine and 30 μl of N-acetyl-ethanolamine were added to the mixture followed by stirring for further 2 hours. After 5 ml of ethyl acetate was added to the reaction mixture, the mixture was washed with water and the resulting organic layer was dried over anhydrous sodium sulfate. The solvent was then distilled off. The residue thus obtained was purified on a preparative silica gel TLC (developing system, toluene-acetone; 1:1) to obtain 3 mg of the authentic (R)-form. The thus obtained authentic (R)-form compound showed the same residence time (14.0 minutes; moving phase 2.5% isopropanol/0.01M phosphate buffer (pH 7.1), flow rate: 0.8 ml/min) as that of the title compound obtained above on the column for optical resolution described above. With respect to the (S)-form, the residence time was 8.4 minutes under the same conditions.

Furthermore, 10.0 mg of this compound was dissolved in 1 ml of methanol solution of 1N sodium methoxide. The solution was heated on an oil bath of 40° C. for 5 hours. Under cooling, 1N hydrochloric acid was added to the reaction mixture to adjust pH to 2. Then 5 ml of distilled water and 5 ml of ethyl acetate were added to the mixture followed by separation. The organic phase was washed with water and then dehydrated over Glauber's salt. The solvent was then distilled off in vacuum. The residue was purified by preparative TCL to give 8.0 mg of the methyl ester. The physicochemical properties of the methyl ester coincided with those of (R)-(−)-1,4-dihydro-2,6-dimethyl-5-methoxycarbonyl-4-(3-nitrophenyl)-3-pyridinecarboxylic acid obtained by the process of Shibanuma et al. described above.

1H-NMR ($CD_3OD$) δ: 8.09 (1H, t, J=2.2 Hz), 7.99 (1H, td, J=8.1, 2.2 & 1.1 Hz), 7.64 (1H, d, J=1.1 Hz), 7.44 (1H, t, J=8.1 Hz), 5.09 (1H, s), 8.62 (3H, s), 2.34 (3H, s), 2.88 (8H, s) $[\alpha]_D^{27}$: −32.0—(c=0.30, methanol) $[\alpha]_D^{27}$: −22.3—(c=0.30, acetone) MS:FAB (neg.) 331 (M—H)

3-2) Preparation of the title compound using other bacteria

Streptomyces sp. A-914 and Streptomyces sp. ATCC 11862 were inoculated, respectively, on medium C (2% potato starch, 2% ESUSAN Meat, 0.5% yeast extract, 0.25% NaCl, 0.32% $CaCO_3$, 0.0005% $FeSO_4$ $7H_2O$, 0.0005% $MnSO_4$ $4H_2O$, 0.0005% $ZnSO_4$ $7H_2O$, pH 7.4) charged in a flask of 250 ml volume followed by incubation at 28° C. for 3 days. After 50 −1 of a solution of 4 mg of 1,4-dihydro-2,6-dimethyl-4-(3-nitrophenyl)pyridine-3,5-dicarboxylic acid bis(2-acetamidoethyl)ester in dimethylsulfoxide was added to 2 ml each of the culture broth obtained. Shaking was continued for further 2 days at 28° C. 1N hydrochloric acid was added to the reaction mixture to adjust pH to 3.0, followed by extraction with ethyl acetate. From the thus obtained organic layer, there were obtained 0.5 mg each of the objective optically active carboxylic acids.

*Helminthosporium zonatum* IFO 6678 and *Botryodiplodia* sp. FI-741 were inoculated, respectively, on medium FI (2% potato starch, 2% ESUSAN Meat, 0.1% $KH_2PO_4$, 0.05% $MgSO_4$ $7H_2O$, 1% glucose, 0.05% Adekanol LG109) followed by incubation at 28° C. for 3 days. A solution of 1,4-dihydro-2,6-dimethyl-4-(3-nitrophenyl)pyridine-3,5-dicarboxylic acid bis(2-acetamidoethyl)ester dihydrochloride in dimethylsulfoxide was added to the culture broth obtained. Shaking was continued for further 2 days at 28° C. Thereafter the culture broth was treated in a manner similar to Example 3-1). The objective monocarboxylic acid was confirmed by TLC analysis.

Industrial Applicability

By the process of the present invention using microorganisms, the compounds represented by general formula (II) or salts thereof can be provided in a simple manner with a high optical purity. The compounds can achieve efficient preparation of optically active 1,4-dihydropyridine derivatives which are effective for ischemic heart diseases or hypertension, e.g., (4R)-(2-nicotinoylamino)ethyl-(3-nitroxy)propyl 1,4-dihydro-2,6-dimethyl-4-(3-nitrophenyl)pyridine-3,5-dicarboxylate (Takahashi et al., Jpn. J. Pharmacol., vol. 58, Supple. I, p399 (1992)) and the like.

We claim:

1. A process for preparing an optically active (4R)-1,4-dihydro-2,6-dimethyl-4-(nitrophenyl)pyridine-3,5-dicarboxylic acid mono-ester derivative which comprises reacting a compound of formula (I) below:

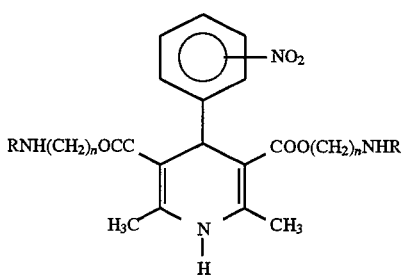

(I)

wherein R represents a lower alkanoyl group, a heterocyclic carbonyl group, a halo-substituted acetyl group, an alkoxyacetyl group, an aryloxyacetyl group, a substituted or unsubstituted phenyl-lower alkanoyl group, a phenyl-substituted or unsubstituted lower alkenoyl group, an alkoxy or alkenyloxycarbonyl group, an aralkyloxycarbonyl group or an organic sulfonyl group; and n represents an integer of 2 to 4, or a salt thereof with a microorganism capable of asymmetric hydrolysis and belonging to the genus Streptomyces, the genus Paecilomyces, the genus Botryodioplodia or the genus Alternaria with lyophilized, dried or immobilized cells of said microorganism, or with a concentrate or dried powder of a culture broth of said microorganism, and collecting the resulting optically active 1,4-dihydropyridine compound of formula (II) below:

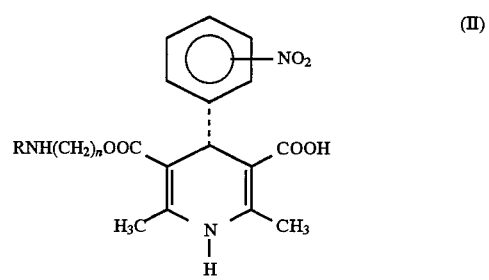

(II)

wherein R and n have the same significance as defined above, or a salt thereof.

2. A 1,4-dihydropyridine compound of formula (III):

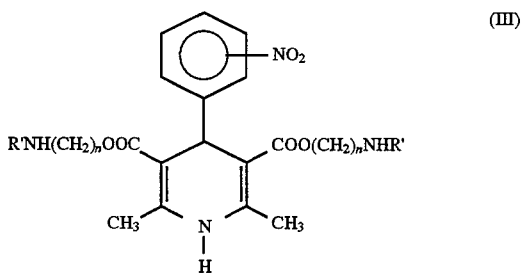

(III)

wherein R' is a lower alkanoyl group and n is an integer of 2 to 4.

3. An optically active 1,4-dihydropyridine compound of formula (IV):

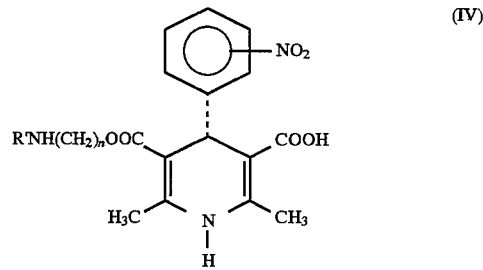

(IV)

wherein R' is a lower alkanoyl group and n is an integer of 2 to 4.

* * * * *

UNITED STATES PATENT AND TRADEMARK OFFICE
CERTIFICATE OF CORRECTION

Page 1 of 2

PATENT NO. : 5,635,395
DATED : June 3, 1997
INVENTOR(S) : ISSHIKI et al

It is certified that error appears in the above-identified patent and that said Letters Patent is hereby corrected as shown below:

Col. 7, line 61, "5" should read --$\delta$--; and line 67, a new paragraph should begin with "FAB-MS".

Col. 8, line 67, a new paragraph should begin with "FAB-MS".

Col. 9, line 45, a new paragraph should begin with "FAB-MS";

line 65, "N-acetyl-ethanolamine" should read --N-acetylethanolamine--.

UNITED STATES PATENT AND TRADEMARK OFFICE
CERTIFICATE OF CORRECTION

PATENT NO. : 5,635,395
DATED : June 3, 1997
INVENTOR(S) : ISSHIKI et al

It is certified that error appears in the above-identified patent and that said Letters Patent is hereby corrected as shown below:

Col. 10, line 34, a new paragraph should begin with "$[\alpha]_D$", both instances; and line 35, a new paragraph should begin with "MS:FAB".

Signed and Sealed this

Seventeenth Day of November, 1998

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,635,395
DATED : June 3, 1997
INVENTOR(S) : ISSHIKI et al

It is certified that error appears in the above-indentified patent and that said Letters Patent is hereby corrected as shown below:

On the title page, "[73] Assignees: Mercian Corporation; Taisho Pharmaceutical Co., Ltd., both of Japan" should read --[73] Assignee: Mercian Corporation, Japan--.

Signed and Sealed this

Sixth Day of July, 1999

Attest:

Q. TODD DICKINSON

Attesting Officer

Acting Commissioner of Patents and Trademarks